United States Patent
Gregg et al.

(10) Patent No.: US 11,181,514 B2
(45) Date of Patent: Nov. 23, 2021

(54) METHODS AND SYSTEMS FOR DETECTING, ALERTING AND ELIMINATING LETHAL GASES

(71) Applicants: Parker Gregg, Roaring Spring, PA (US); Cayden Wright, Roaring Spring, PA (US)

(72) Inventors: Parker Gregg, Roaring Spring, PA (US); Cayden Wright, Roaring Spring, PA (US)

( * ) Notice: Subject to any disclaimer, the term of this patent is extended or adjusted under 35 U.S.C. 154(b) by 360 days.

(21) Appl. No.: 16/266,955

(22) Filed: Feb. 4, 2019

(65) Prior Publication Data
US 2020/0249213 A1 Aug. 6, 2020

(51) Int. Cl.
| | |
|---|---|
| *G01N 33/00* | (2006.01) |
| *F24F 11/30* | (2018.01) |
| *G08B 21/14* | (2006.01) |
| *B60R 99/00* | (2009.01) |
| *G07C 5/00* | (2006.01) |
| *F24F 110/70* | (2018.01) |

(52) U.S. Cl.
CPC .......... *G01N 33/004* (2013.01); *B60R 99/00* (2013.01); *F24F 11/30* (2018.01); *G07C 5/008* (2013.01); *G08B 21/14* (2013.01); *F24F 2110/70* (2018.01)

(58) Field of Classification Search
CPC ....... G01N 33/004; F24F 11/30; G08B 21/14; B60R 99/00; G07C 5/008
See application file for complete search history.

(56) References Cited

U.S. PATENT DOCUMENTS

| | | | | |
|---|---|---|---|---|
| 5,526,280 | A * | 6/1996 | Consadori | G01N 27/16 340/632 |
| 5,564,626 | A * | 10/1996 | Kettler | F24F 8/10 236/49.3 |
| 10,131,362 | B1 * | 11/2018 | Gingrich | G08B 23/00 |
| 2007/0200719 | A1 * | 8/2007 | Adkins | G01N 33/004 340/632 |
| 2010/0042333 | A1 * | 2/2010 | Scheffler | G01N 33/004 702/24 |
| 2014/0365100 | A1 * | 12/2014 | Speier | F02D 17/04 701/101 |
| 2016/0075296 | A1 * | 3/2016 | Alderman | G08G 1/205 340/989 |
| 2017/0057319 | A1 * | 3/2017 | Renke | B60H 1/008 |
| 2018/0370430 | A1 * | 12/2018 | Gage, III | B60Q 9/00 |

* cited by examiner

*Primary Examiner* — Hongmin Fan
(74) *Attorney, Agent, or Firm* — Arent Fox LLP

(57) ABSTRACT

Methods, systems, and computer-readable mediums storing computer executable code for detecting and alerting of gases is provided. The method may include determining a parts per million of a specified gas. The method may also include comparing the determined parts per million to a pre-determined threshold. The method may include, when the parts per million meets or exceeds a threshold, generating a control signal. The method may also include transmitting the control signal to an alerting device to emit an alert to a user. The method may also include transmitting the control signal to a control device, wherein the control device performs a specified task.

20 Claims, 6 Drawing Sheets

METHODS AND SYSTEMS FOR DETECTING, ALERTING AND ELIMINATING LETHAL GASES

TECHNICAL FIELD

The subject matter disclosed herein relates to systems and methods for alerting and eliminating gases from a location and, more particularly, to the alerting of users and/or disabling the source emitting the gases if a detection of lethal gas reaches specific levels.

BACKGROUND

Many gases are lethal for humans, for example, arsenic pentafluoride, arsine, bis(trifluoromethyl), boron tribromide, boron trichloride, boron trifluoride, bromine, bromine chloride, bromomethane, carbon monoxide, chlorine, chlorine pentafluoride, chlorine trifluoride, chloropicrin, cyanogen, cyanogen chloride, diazomethane, diborane, dichloroacetylene, dichlorosilane, fluorine, formaldehyde (anhydrous), germane, hexaethyl tetraphosphate, hydrogen azide, hydrogen cyanide, hydrogen selenide, hydrogen sulfide, hydrogen telluride, nickel tetracarbonyl, nitrogen dioxide, osmium tetroxide, oxygen difluoride, perchloryl fluoride, perfluoroisobutylene, phosgene, phosphine, phosphorus pentafluoride, selenium hexafluoride, silicon tetrachloride, silicon tetrafluoride, stibine, disulfur decafluoride, sulfur tetrafluoride, tellurium hexafluoride, tetraethyl pyrophosphate, tetraethyl dithiopyrophosphate, trifluoroacetyl chloride, and tungsten hexafluoride. Some of these gases occur naturally, while others occur through man-made combinations. Some of these gases have strong odors, while others, for example, carbon monoxide, have no odor at all. When some of these gases reach lethal levels of parts per million ("PPM") for humans, it may be too late for a human to react and reach safety. Conventional sensors design alert humans when some of these gases reach lethal levels, but it may be too late for the human to get themselves to safety, by either determining the source of the gas or removing themselves from the deadly situation.

In view of the foregoing, a lethal gas detection, alert and disabling system and method that is easier, more responsive and automated may be desirable. Further advantages will become apparent from the disclosure provided below.

SUMMARY

This summary is provided to introduce a selection of concepts in a simplified form that are further described below in the DETAILED DESCRIPTION. This summary is not intended to identify key features of the claimed subject matter, nor is it intended to be used as an aid in determining the scope of the claimed subject matter.

In an aspect, the disclosure provides a lethal gas detection, alerting and disabling system. The system may include a memory and at least one processor coupled with the memory and configured to determine a parts per million of a specified gas. The system may also be configured to compare the determined parts per million to a pre-determined threshold. The system may also be configured to, when the parts per million meets or exceeds a threshold, generate a control signal. The system may also be configured to transmit the control signal to an alerting device to emit an alert to a user. The system may also be configured to transmit the control signal to a control device, wherein the control device performs a specified task.

In an aspect, the disclosure provides a method for detecting a lethal gas, alerting a user, and disabling the source generating the lethal gas. The method may include determining a parts per million of a specified gas. The method may also include comparing the determined parts per million to a pre-determined threshold. The method may include, when the parts per million meets or exceeds a threshold, generating a control signal. The method may also include transmitting the control signal to an alerting device to emit an alert to a user. The method may also include transmitting the control signal to a control device, wherein the control device performs a specified task.

In another aspect, the disclosure provides a non-transitory computer-readable medium including instructions that when executed by a processor may cause the processor to detect a lethal gas, alert a user and disable the source generating the lethal gas. The non-transitory computer-readable medium including instructions that when executed by a processor may cause the processor to determine a parts per million of a specified gas. The non-transitory computer-readable medium including instructions that when executed by a processor may cause the processor to compare the determined parts per million to a pre-determined threshold. The non-transitory computer-readable medium including instructions that when executed by a processor may cause the processor to, when the parts per million meets or exceeds a threshold, generate a control signal. The non-transitory computer-readable medium including instructions that when executed by a processor may cause the processor to transmit the control signal to an alerting device to emit an alert to a user. The non-transitory computer-readable medium including instructions that when executed by a processor may cause the processor to transmit the control signal to a control device, wherein the control device performs a specified task.

BRIEF DESCRIPTION OF THE DRAWINGS

The novel features believed to be characteristic of the disclosure are set forth in the appended claims. In the descriptions that follow, like parts are marked throughout the specification and drawings with the same numerals, respectively. The drawing figures are not necessarily drawn to scale and certain figures may be shown in exaggerated or generalized form in the interest of clarity and conciseness. The disclosure itself, however, as well as a preferred mode of use, further objects and advances thereof, will be best understood by reference to the following detailed description of illustrative aspects of the disclosure when read in conjunction with the accompanying drawings, wherein:

DETAILED DESCRIPTION

Figure 1:
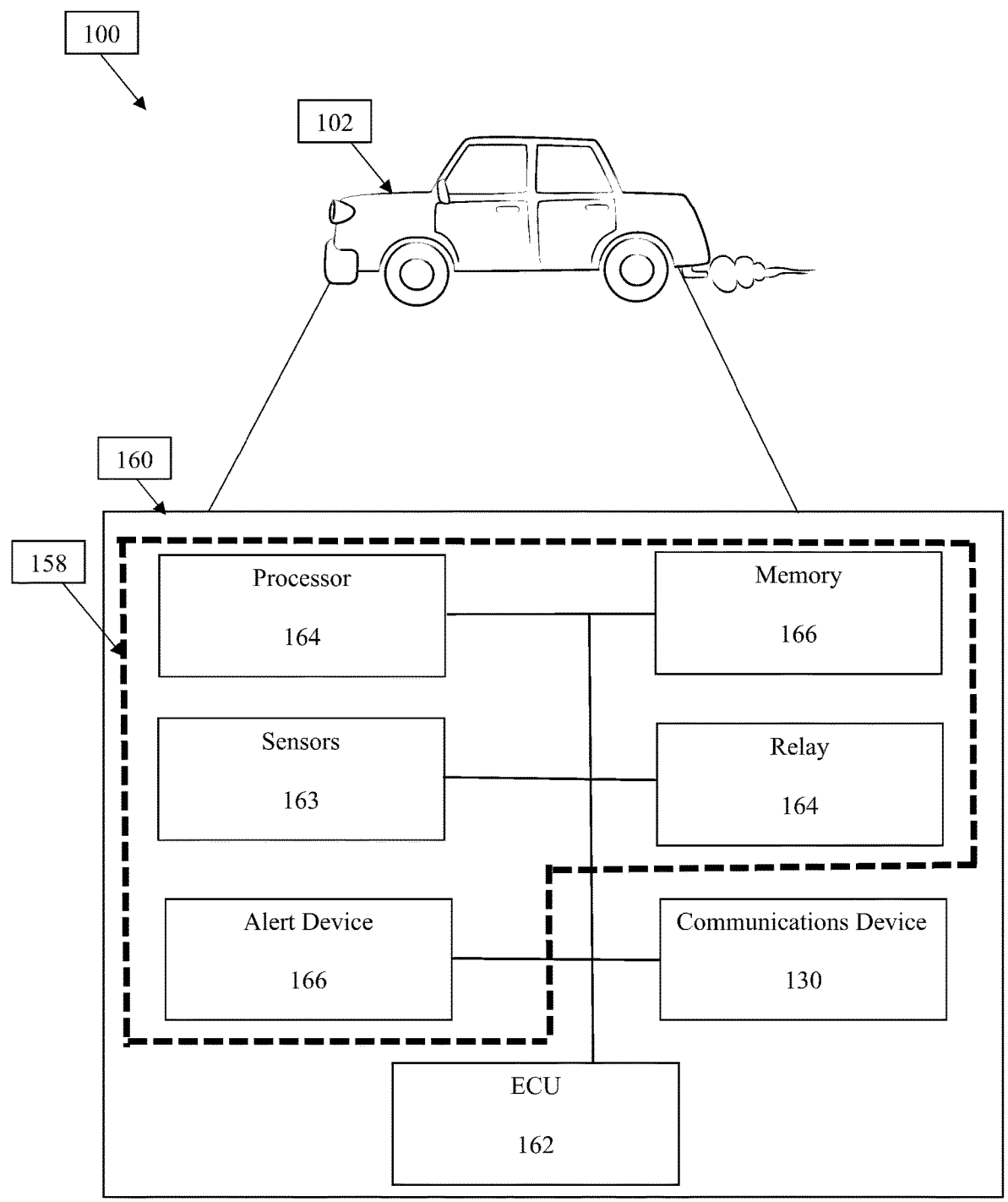
FIG. 1 illustrates a schematic view of an example vehicle system in accordance with aspects of the present disclosure.

The following includes definitions of selected terms employed herein. The definitions include various examples and/or forms of components that fall within the scope of a term and that may be used for implementation. The examples are not intended to be limiting.

A "processor," as used herein, processes signals and performs general computing and arithmetic functions. Signals processed by the processor may include digital signals, data signals, computer instructions, processor instructions, messages, a bit, a bit stream, or other computing that may be received, transmitted and/or detected.

A "bus," as used herein, refers to an interconnected architecture that is operably connected to transfer data between computer components within a singular or multiple systems. The bus may be a memory bus, a memory controller, a peripheral bus, an external bus, a crossbar switch, and/or a local bus, among others. The bus may also be a vehicle bus that interconnects components inside a vehicle using protocols, such as Controller Area network (CAN), Local Interconnect Network (LIN), among others.

A "memory," as used herein may include volatile memory and/or non-volatile memory. Non-volatile memory may include, for example, ROM (read only memory), PROM (programmable read only memory), EPROM (erasable PROM) and EEPROM (electrically erasable PROM). Volatile memory may include, for example, RAM (random access memory), synchronous RAM (SRAM), dynamic RAM (DRAM), synchronous DRAM (SDRAM), double data rate SDRAM (DDR SDRAM), and/or direct RAM bus RAM (DRRAM).

An "operable connection," as used herein may include a connection by which entities are "operably connected", is one in which signals, physical communications, and/or logical communications may be sent and/or received. An operable connection may include a physical interface, a data interface and/or an electrical interface.

A "vehicle," as used herein, refers to any moving vehicle that is powered by any form of energy. A vehicle may carry human occupants or cargo. The term "vehicle" includes, but is not limited to cars, trucks, vans, minivans, SUVs, motorcycles, scooters, boats, personal watercraft, and aircraft. In some cases, a motor vehicle includes one or more engines.

The term "graphical user interface," "GUI," or "user interface," as used herein, can refer to a type of interface that allows users to interact with electronic devices, the vehicle system, the vehicle, vehicle applications or the like, through graphical icons, visual indicators such as secondary notation, text-based, type command labels, text navigation, and the like.

The term "screen," "display screen," or "display," as used herein, can refer to a surface area upon which text, graphics and video are temporarily made to appear for human viewing. These may include, but are not limited to, eidophor, electroluminescent display ("ELD"), electronic paper, e-Ink, gyricon, light emitting diode display ("LED"), cathode ray tube ("CRT"), liquid-crystal display ("LCD"), plasma display panel ("PDP"), digital light processing ("DLP"), and the like.

The term "lethal gas," as used herein, can refer to any gas that may be considered harmful to a human at any level. These may include, but are not limited to arsenic pentafluoride, arsine, bis(trifluoromethyl), boron tribromide, boron trichloride, boron trifluoride, bromine, bromine chloride, bromomethane, carbon monoxide, chlorine, chlorine pentafluoride, chlorine trifluoride, chloropicrin, cyanogen, cyanogen chloride, diazomethane, diborane, dichloroacetylene, dichlorosilane, fluorine, formaldehyde (anhydrous), germane, hexaethyl tetraphosphate, hydrogen azide, hydrogen cyanide, hydrogen selenide, hydrogen sulfide, hydrogen telluride, nickel tetracarbonyl, nitrogen dioxide, osmium tetroxide, oxygen difluoride, perchloryl fluoride, perfluoroisobutylene, phosgene, phosphine, phosphorus pentafluoride, selenium hexafluoride, silicon tetrachloride, silicon tetrafluoride, stibine, disulfur decafluoride, sulfur tetrafluoride, tellurium hexafluoride, tetraethyl pyrophosphate, tetraethyl dithiopyrophosphate, trifluoroacetyl chloride, and tungsten hexafluoride.

In an aspect, the present disclosure provides systems and methods for detection of a lethal gas emitted from a variety of sources. For example, some sources that emit the lethal gas carbon monoxide may include fuel-burning devices such as boilers, furnaces, water heaters, fireplaces, charcoal grills, gas and kerosene heaters, gas and wood stoves, clothes dryers and internal combustion engine vehicles. Further, some outdoor objects that emit the lethal gas carbon monoxide may include camp stoves, open fire, barbeques, lawnmowers, generators, motors vehicles and power tools that contain internal combustion engines. Cigarette and cigar smoking is a common source of carbon monoxide. Although carbon monoxide will be used as merely an example throughout the specification when describing the systems and methods, note that any lethal gas may be applied.

Turning to FIG. 1, an example vehicle system 100, which comprises an example vehicle 102, is schematically illustrated. The vehicle 102 may be an internal combustion engine vehicle producing a lethal gas. In an aspect, the vehicle 102 may include a vehicle control system 160 that controls the operation of the internal combustion engine and the monitoring of lethal levels of carbon monoxide.

The vehicle control system 160 may reside within the vehicle 100. The components of the vehicle control system 160, as well as the components of other systems, hardware architectures, and software architectures discussed herein, may be combined, omitted or organized into various implementations. A subset of the vehicle control system 160 may be the alert detection system 158. The alert detection system comprises a processor 164, memory 166, sensors 163, a relay 164, and an alert device 166. The alert detection system will be described further below. In one aspect of the invention, the alert detection system 158 may be a separate self-contained unit that may be able to be placed in or connected to any type of device that may generate or be exposed to a lethal gas. For example, the alert detection system 158 may be placed in or connected to homes, campers/mobile homes, factories, furnaces and generators, as some non-liming examples.

The vehicle control system 160 may generally include, in addition to the alert detection system 158, an electronic control unit (ECU) 162 that operably controls a plurality of vehicle systems. The vehicle systems may include, but are not limited to a suspension control system, a steering control system, an acceleration control system, and the fuel pump to the internal combustion engine. The vehicle control system 160 may also include a processor 164 and a memory 166 that communicate with the ECU 162, and a communication device 130.

The ECU 162 may include internal processing memory, an interface circuit, and bus lines for transferring data, sending commands, and communicating with the vehicle systems. The ECU 162 may include an internal processor and memory, not shown. The vehicle 102 may also include a bus for sending data internally among the various components of the vehicle control system 160.

The memory 166 may store instructions executable by the processor 164 for carrying out the methods described herein. Further, the memory 166 may store parameters for carrying out the methods described herein. For example, the memory 166 may store software executable by the processor 164 for operating the vehicle control system 160.

The vehicle 102 may further include a communications device 130 (e.g., wireless modem) for providing wired or wireless computer communications utilizing various protocols to send/receive electronic signals internally with respect to features and systems within the vehicle 102 and with respect to external devices. These protocols may include a wireless system utilizing radio-frequency (RF) communications (e.g., IEEE 802.11 (Wi-Fi), IEEE 802.15.1 (Bluetooth®)), a near field communication system (NFC) (e.g., ISO 13157), a local area network (LAN), a wireless wide area network (WWAN) (e.g., cellular) and/or a point-to-point system. Additionally, the communications device 130 of the vehicle 102 may be operably connected for internal computer communication via a bus (e.g., a CAN or a LIN protocol bus) to facilitate data input and output between the electronic control unit 112 and vehicle features and systems. In an aspect, the communications device 130 may be configured for vehicle-to-vehicle (V2V) communications. For example, V2V communications may include wireless communications over a reserved frequency spectrum. As another example, V2V communications may include an ad hoc network between vehicles set up using Wi-Fi or Bluetooth®.

As discussed above, the vehicle control system 160 may comprise sensors 163 for detection of various lethal gases. The sensors may be located within or outside any aspect of the vehicle 102. For example, one sensor may be located within an internal combustion engine compartment, and a second sensor may be located on the frame of the vehicle. In another example, one sensor may be located near the exhaust of the vehicle, and a second sensor may be located in the interior of the vehicle. The sensors 163 may be a MQ-7 gas sensor that detects carbon monoxide, but other sensors depending upon the type of lethal gas detected may be used.

As discussed above, the vehicle control system 160 comprises an alert device 166 that produces at least one of light or noise based upon a signal. The alert device may be located within or outside any aspect of the vehicle 102. For example, the alert device may be located within the interior of the vehicle or may be located on the exterior of the frame of the vehicle. The alert device 163 may be triggered to operate based upon predetermined thresholds of detection by the sensors 163. The alert device 166 may be a piezo buzzer or a strobe light, but other alert devices may be implemented based upon the type of alert desired. Further, the alert device may be a combination of both audible and visual notifications to a user.

Figure 2:
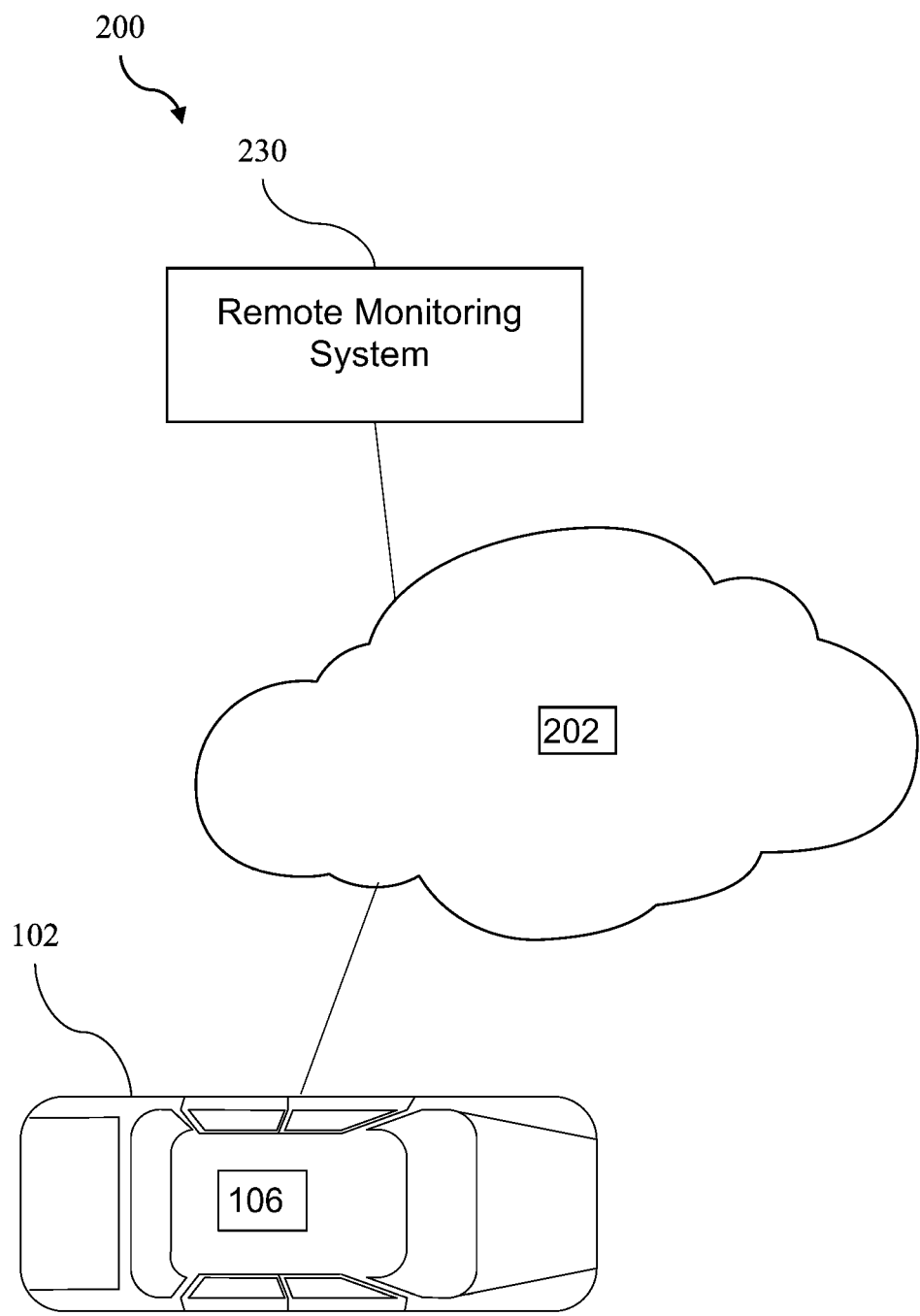
FIG. 2 illustrates a conceptual diagram illustrating a network in accordance with aspects of the present disclosure.

FIG. 2 illustrates an example network 200 for monitoring the vehicle control system 160. The network 202 may be a communications network that facilitates communications between multiple systems. For example, the network 202 may include the Internet or another internet protocol (IP) based network. The network 202 may enable the vehicle control system 160 to communicate with a remote monitoring system 230. The vehicle control system 160, within the vehicle 102, may communicate with the network 202 via the communications device 130. The communications device may, for example, transmit signals to the remote monitoring system 230. The signals transmitted to the remote monitoring system 230 may be notifications that the alert detection system has detected specific PPM of a lethal gas. In one aspect of the invention, the signals may provide notifications to the remote monitoring system 230, that the alert detection system has detected carbon monoxide in the air, via the sensors 163, at or between 400 ppm to 800 ppm (thresholds). In another aspect, aspect of the invention, the signals may provide notifications to the remote monitoring system 230, that the alert detection system has detected carbon monoxide in the air, via the sensors 163, at or above 800 ppm. Other thresholds may be set depending upon the lethal gas being detected. The threshold amounts of ppm may be predetermined based upon the type of lethal gas being detected.

Further, the remote monitoring system 160 may receive distinct signals transmitted by the vehicle control system 160. For example, if the alert detection system 158 is implemented for carbon monoxide, as described above, one distinct signal may be transmitted based upon the sensors detecting gases to be within the first threshold range, which is between 400 ppm to 800 ppm. This may be considered signal 1. In another example, if the alert detection system 158 is implemented for carbon monoxide, as described above, a second distinct signal may be transmitted based upon the sensors detecting gases to be within the second threshold range, which is between 801 ppm to 5000 ppm. This may be considered signal 2. The processing of the different signals will be described below.

The remote monitoring system 230 may include a computer system, as shown with respect to FIG. 7 and further described below, associated with one or more call centers, monitoring stations or data centers. The remote monitoring system 230 may include one or more databases that store data collected from users, for example, emergency contact information, medical history, allergies, etc. The remote monitoring system 230 may also include a memory that stores instructions for executing processes for performing instance segmentation and a processor configured to execute the instructions.

In one aspect of the invention, based upon the type of received signal at the remote monitoring system 230, different actions may be performed. Some actions that may be performed are contacting local authorities, contacting family members, contacting police, contacting EMS, etc. In another aspect, some actions that may be performed are performed remotely, for example, opening a window, turning on or off a HVAC system, opening a garage door, shutting off the device emitting the lethal gas, etc. The contacting may be performed via text, telephone, automated call, Wi-Fi, cellular, or a direct alert. For example, if signal 1, as described above, is received by the remote monitoring system, family members may be contacted and a garage door is opened at location of the vehicle 102. In another example, if signal 2, as described above, is received by the remote monitoring system, police, EMS and family members may be contacted and the vehicle 102 emitting the lethal gas is shut off.

In one aspect of the invention, as described above, the ECU 162 of FIG. 1 may receive a signal via the communication device 130, transmitted from the remote monitoring system 230 instructing the ECU 162 to shut off the vehicle 102. In another aspect, the alert detection system 158 may directly send a signal to the ECU 162 to shut off the vehicle 102 upon determination by the sensors 163 that a first or second threshold has been met by the ppm of a lethal gas. Further, in conjunction with shutting off the vehicle 102, or separately, the alert device 166 may be contacted directly via the alert detection system 158, or remotely, via the remote monitoring system 158, to emit a visual or audible alert.

Figure 3:
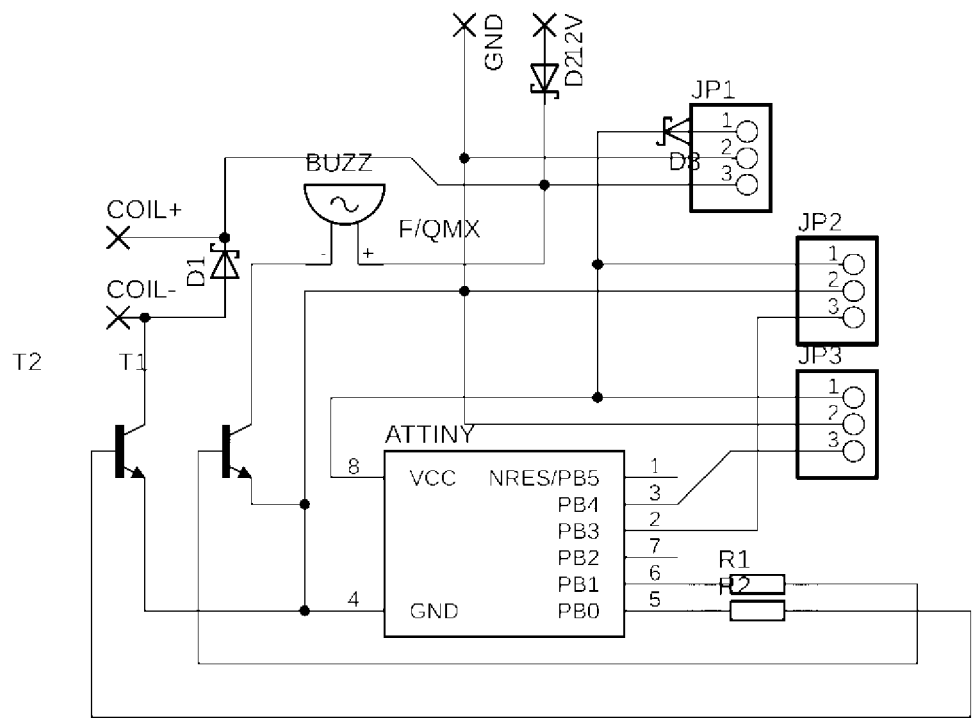
FIG. 3 illustrates a circuit diagram in accordance with aspects of the present disclosure.

Turning to FIG. 3, a circuit diagram is disclosed illustrating portions of the alert detection system 158. For example, the circuit diagram illustrates a non-limiting example of the connections between portions of the alert detection system 158.

Figure 4:
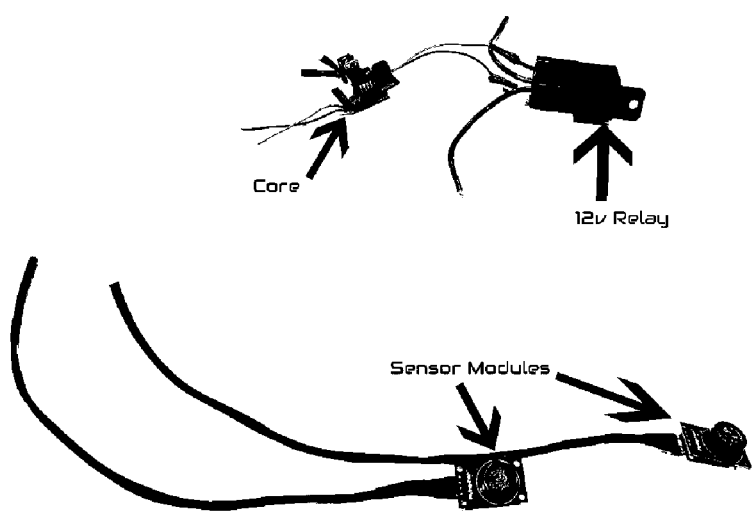
FIG. 4 illustrates a photograph of a portion of the alert detection system, in accordance with aspects of the present disclosure.

Turning to FIG. 4, a photograph-illustrating portion of the alert detection system 158. For example, the core may comprise portions of the alert detection system 158 such as the processor 164, the memory 166 and the alert device 166. Further, FIG. 4 illustrates the sensors 163 and the relay 164 of the alert detection system 158. These examples are not intended to be limiting.

Figure 5:
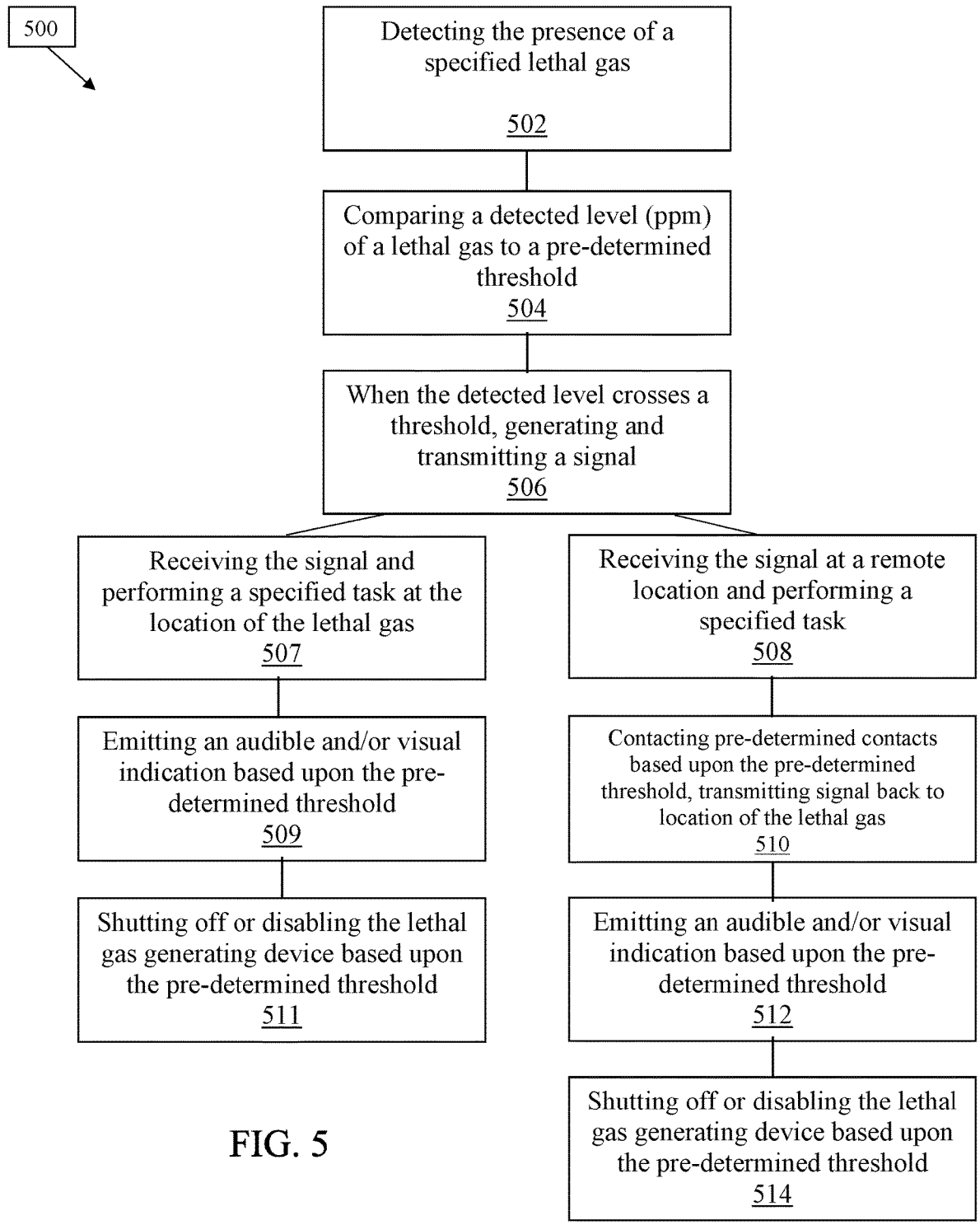
FIG. 5 illustrates a flowchart showing an example method of detecting, alerting and eliminating lethal gases in accordance with aspects of the present disclosure.

Turning to FIG. 5, illustrates a flowchart of an example method of detecting, alerting and eliminating lethal gases. The method 500 may be performed by the vehicle control system 160 within a vehicle 102 and/or a separate self-contained alert detection system 158, as described above.

At block 502, the method 500 may include detecting the presence of a specified lethal gas. For example, the sensors 163 described in FIG. 1 above, may be activated to determine the presence of a specific lethal gas. The lethal gas may be determined based upon parts per million ("ppm") value.

At block 504, the method 500 may include comparing a detected level (ppm) of a lethal gas to a pre-determined threshold. For example, the sensors 163 of FIG. 1 may transmit the determined ppm value to the processor 164 to be compared against a pre-determined threshold. As described above in relation to carbon monoxide, the ppm may have two-separate and distinct threshold, but additional thresholds may be pre-determined.

At block 506, the method 500 may include when the detected level crosses a threshold, generating and transmitting a signal. For example, as described above in relation to carbon monoxide, the detected ppm is compared to the lowest threshold of 400 ppm. Once the threshold has been met or exceeded, the processor may send a signal to either the ECU 162 or the communications device 130 of FIG. 1.

At block 507, the method 500 may include receiving the signal and performing a specified task at the location of the lethal gas. For example, the ECU 162, as described above, may receive the signal and perform a specified task. The task, for example, may be adjusting the ratio of gasoline to air within the vehicle 102 to lower the lethal gas level or turning on the HVAC. In another aspect, the task may be to disable the engine of the vehicle 102, described below.

At block 508, the method 500 may include receiving the signal at a remote location and performing a specified task. For example, as described above, the signal may be received by the remote monitoring system 230 of FIG. 2. The tasks may be different based upon the threshold the ppm exceeds.

At block 509, the method 500 may include emitting an audible and/or visual indication based upon the pre-determined threshold. For example, as described above, the alert device 166 may be activated by the ECU 162 based upon the threshold exceeded.

At block 510, the method 500 may include contacting pre-determined contacts based upon the pre-determined threshold, transmitting signal back to location of the lethal gas. For example, as described above, the remote monitoring system 230 may remotely contact predetermined contacts such as the police or family members based upon the threshold exceeded.

At block 511, the method 500 may include shutting off or disabling the lethal gas-generating device based upon the pre-determined threshold. For example, as described above, the ECU may proceed with disabling the engine of the vehicle 102 based upon the threshold exceeded.

At block 512, the method 500 may include emitting an audible and/or visual indication based upon the pre-determined threshold. This step is comparable to block 509 described above.

At block 514, the method 500 may include shutting off or disabling the lethal gas-generating device based upon the pre-determined threshold. This step is comparable to block 511 described above.

Figure 6:
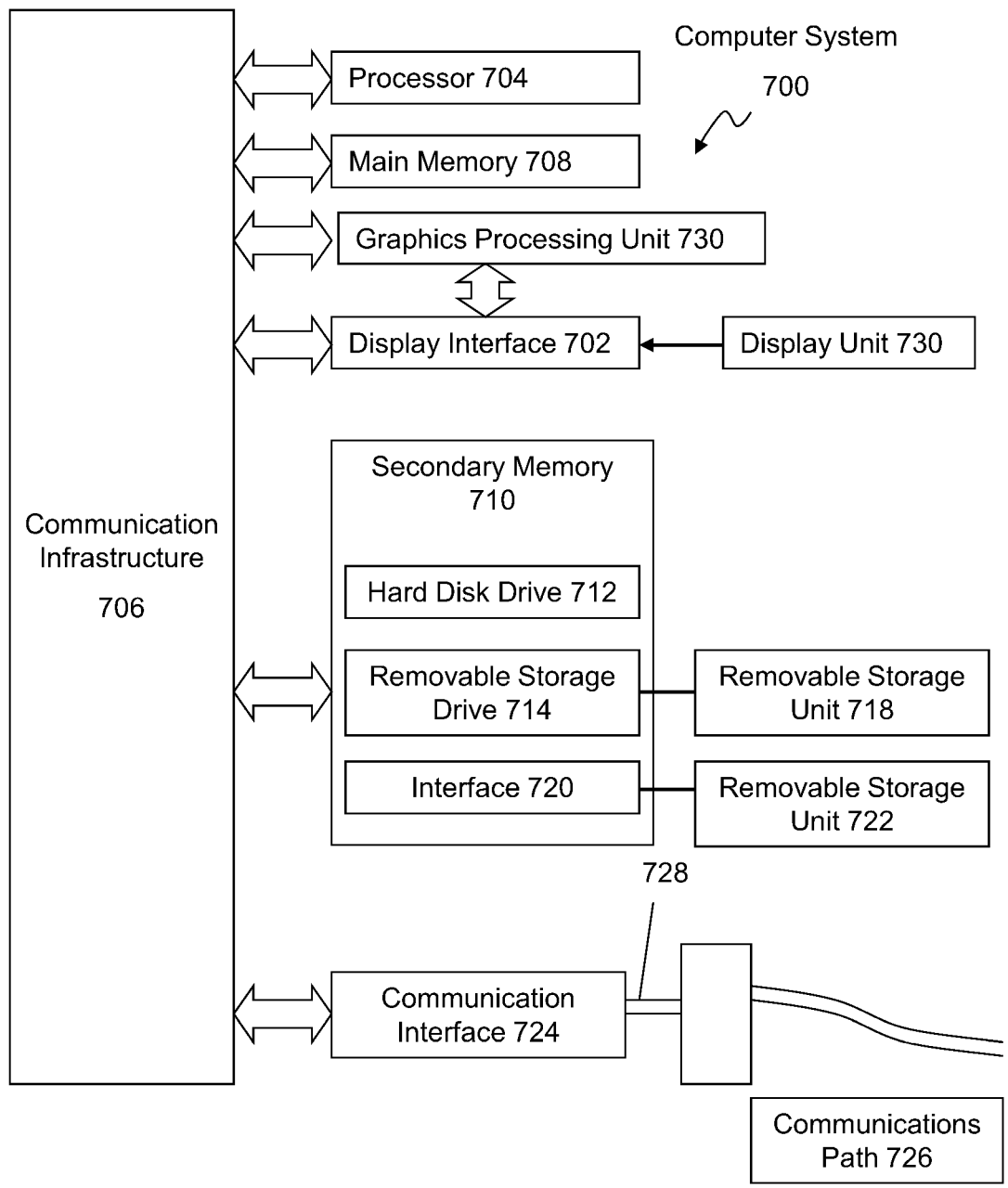
FIG. 6 presents an exemplary system diagram of various hardware components and other features for use in accordance with aspects of the present disclosure.

Aspects of the present disclosure may be implemented using hardware, software, or a combination thereof and may be implemented in one or more computer systems or other processing systems. In one aspect, the disclosure is directed toward one or more computer systems capable of carrying out the functionality described herein. For example, the computer system may implement the vehicle control system 160. FIG. 6 presents an example system diagram of various hardware components and other features that may be used in accordance with aspects of the present disclosure. Aspects of the present disclosure may be implemented using hardware, software, or a combination thereof and may be implemented in one or more computer systems or other processing systems. In one exemplary variation, aspects of the disclosure are directed toward one or more computer systems capable of carrying out the functionality described herein. An example of such a computer system 700 as shown in FIG. 6.

Computer system 700 includes one or more processors, such as processor 704. The processor 704 is connected to a communication infrastructure 706 (e.g., a communications bus, cross-over bar, or network). Various software aspects are described in terms of this example computer system. After reading this description, it will become apparent to a person skilled in the relevant art(s) how to implement aspects of the disclosure using other computer systems and/or architectures.

Computer system 700 may include a display interface 702 that forwards graphics, text, and other data from the communication infrastructure 706 (or from a frame buffer not shown) for display on a display unit 730. Computer system 700 also includes a main memory 708, preferably random access memory (RAM), and may include a secondary memory 710. The secondary memory 710 may include, for example, a hard disk drive 712 and/or a removable storage drive 714, representing a floppy disk drive, a magnetic tape drive, an optical disk drive, etc. The removable storage drive 714 reads from and/or writes to a removable storage unit 718 in a well-known manner. Removable storage unit 718, represents a floppy disk, magnetic tape, optical disk, etc., which is read by and written to removable storage drive 714. As will be appreciated, the removable storage unit 718 includes a computer usable storage medium having stored therein computer software and/or data.

In alternative aspects, secondary memory 710 may include other similar devices for allowing computer programs or other instructions to be loaded into computer system 700. Such devices may include, for example, a removable storage unit 722 and an interface 720. Examples of such may include a program cartridge and cartridge interface (such as that found in video game devices), a removable memory chip (such as an erasable programmable read only memory (EPROM), or programmable read only memory (PROM)) and associated socket, and other removable storage units 722 and interfaces 720, which allow software and data to be transferred from the removable storage unit 722 to computer system 700.

Computer system 700 may also include a communications interface 724. Communications interface 724 allows software and data to be transferred between computer system 700 and external devices. Examples of communications interface 724 may include a modem, a network interface (such as an Ethernet card), a communications port, a Personal Computer Memory Card International Association (PCMCIA) slot and card, etc. Software and data transferred via communications interface 724 are in the form of signals 728, which may be electronic, electromagnetic, optical or other signals capable of being received by communications interface 724. These signals 728 are provided to communications interface 724 via a communications path (e.g., channel) 726. This path 726 carries signals 728 and may be implemented using wire or cable, fiber optics, a telephone line, a cellular link, a radio frequency (RF) link and/or other communications channels. In this document, the terms "computer program medium" and "computer usable medium" are used to refer generally to media such as a removable storage drive 780, a hard disk installed in hard disk drive 770, and signals 728. These computer program products provide software to the computer system 700. Aspects of the disclosure are directed to such computer program products.

Computer programs (also referred to as computer control logic) are stored in main memory 708 and/or secondary memory 710. Computer programs may also be received via communications interface 724. Such computer programs, when executed, enable the computer system 700 to perform various features in accordance with aspects of the present disclosure, as discussed herein. In particular, the computer programs, when executed, enable the processor 704 to perform such features. Accordingly, such computer programs represent controllers of the computer system 700.

In variations where aspects of the disclosure are implemented using software, the software may be stored in a computer program product and loaded into computer system 700 using removable storage drive 714, hard disk drive 712, or communications interface 720. The control logic (software), when executed by the processor 704, causes the processor 704 to perform the functions in accordance with aspects of the disclosure as described herein. In another variation, aspects are implemented primarily in hardware using, for example, hardware components, such as application specific integrated circuits (ASICs). Implementation of the hardware state machine so as to perform the functions described herein will be apparent to persons skilled in the relevant art(s).

In yet another example variation, aspects of the disclosure are implemented using a combination of both hardware and software.

Figure 7:
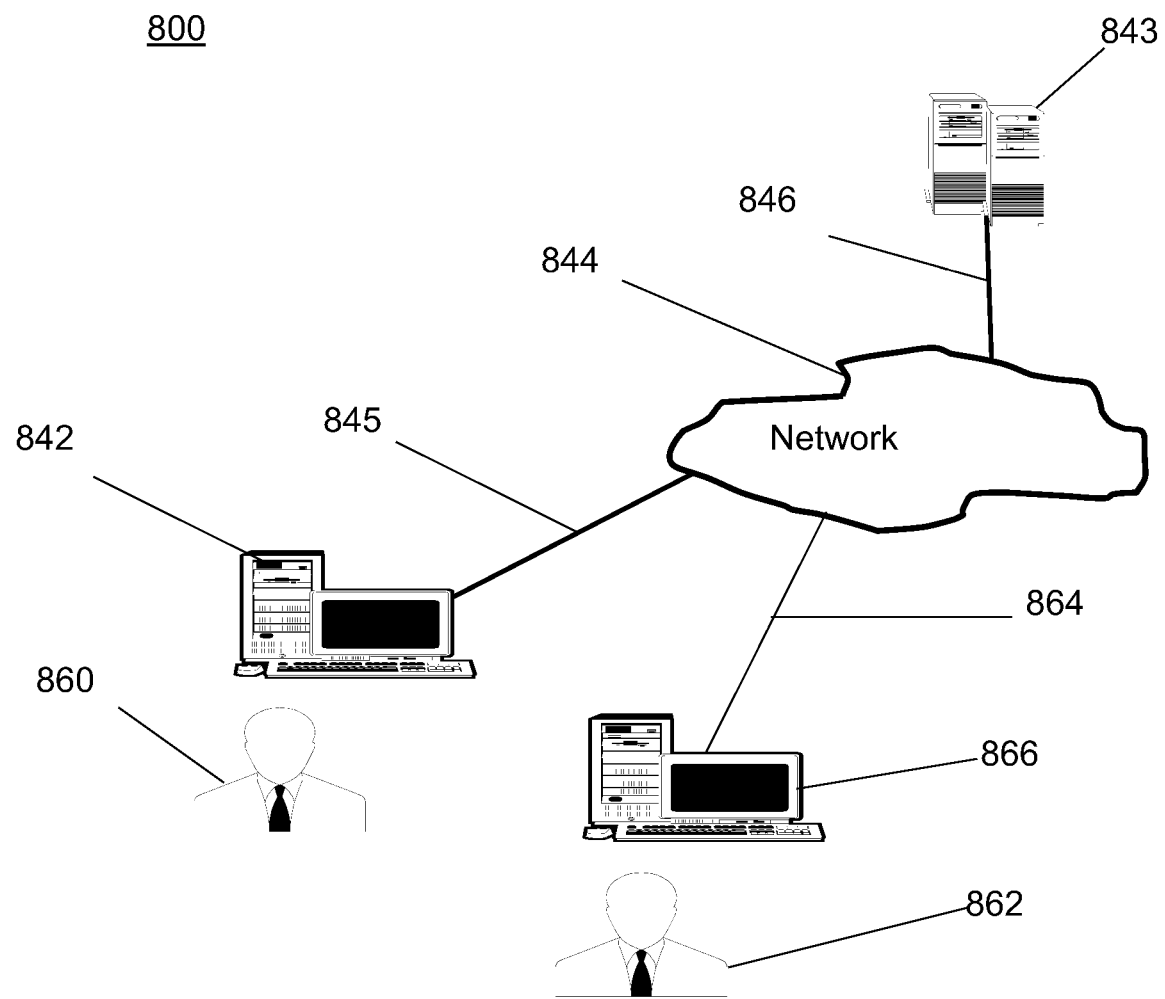
FIG. 7 is a block diagram of various exemplary system components for use in accordance with aspects of the present disclosure.

FIG. 7 is a block diagram of various example system components that may be used in accordance with aspects of the present disclosure. For example, the various components may be within the vehicle 102, or only some of the components may be within the vehicle 102, and other components may be remote from the vehicle 102. The system 800 includes one or more accessors 860, 862 (also referred to interchangeably herein as one or more "users") and one or more terminals 842, 866 (such terminals may be or include, for example, various features of the vehicle control system 160 or the platform control system 260). In one aspect, data for use in accordance with aspects of the present disclosure is, for example, input and/or accessed by accessors 860, 862 via terminals 842, 866, such as personal computers (PCs), minicomputers, mainframe computers, microcomputers, telephonic devices, or wireless devices, such as personal digital assistants ("PDAs") or a hand-held wireless devices coupled to a server 843, such as a PC, minicomputer, mainframe computer, microcomputer, or other device having a processor and a repository for data and/or connection to a repository for data, via, for example, a network 844, such as the Internet or an intranet, and couplings 845, 846, 864. The couplings 845, 846, 864 include, for example, wired, wireless, or fiber optic links. In another example variation, the method and system in accordance with aspects of the present disclosure operate in a stand-alone environment, such as on a single terminal.

The aspects of the disclosure discussed herein may also be described and implemented in the context of computer-readable storage medium storing computer-executable instructions. Computer-readable storage media includes computer storage media and communication media. For example, flash memory drives, digital versatile discs (DVDs), compact discs (CDs), floppy disks, and tape cassettes. Computer-readable storage media may include volatile and nonvolatile, removable and non-removable media implemented in any method or technology for storage of information such as computer readable instructions, data structures, modules or other data.

It will be appreciated that various implementations of the above-disclosed and other features and functions, or alternatives or varieties thereof, may be desirably combined into many other different systems or applications. Also that various presently unforeseen or unanticipated alternatives, modifications, variations, or improvements therein may be subsequently made by those skilled in the art which are also intended to be encompassed by the following claims.

What is claimed is:

1. A method of detecting and alerting of gases comprising:
determining a parts per million of a specified gas;
comparing the determined parts per million to a pre-determined threshold;
when the determined parts per million meets or exceeds the pre-determined threshold, generating a control signal,
transmitting the control signal to an alerting device to emit an alert to a user; and
transmitting the control signal to a control device, wherein the control device performs a specified task,
when the determined parts per million meets or exceeds a second threshold, transmitting an additional control signal to a remote server;
wherein the remote server contacts emergency services,
wherein the pre-determined threshold is between 400 parts per million and 800 parts per million, and the second threshold is at or above 800 parts per million.

2. The method of claim 1, wherein the specified gas is carbon monoxide, and wherein the specified task comprises disabling an internal combustion engine located within a vehicle.

3. The method of claim 1, wherein the alerting device is a piezo buzzer.

4. The method of claim 1, wherein the parts per million is determined by a plurality of sensors, and wherein at least one sensor is located at a position where the specified gas is emitted.

5. The method of claim 1, wherein the specified task includes at least one of opening a window, turning on or off a HVAC system, opening a garage door, or shutting off a device emitting the specified gas.

6. The method of claim 1, wherein the specified gas is at least one of arsenic pentafluoride, arsine, bis(trifluoromethyl), boron tribromide, boron trichloride, boron trifluoride, bromine, bromine chloride, bromomethane, carbon monoxide, chlorine, chlorine pentafluoride, chlorine trifluoride, chloropicrin, cyanogen, cyanogen chloride, diazomethane, diborane, dichloroacetylene, dichlorosilane, fluorine, formaldehyde (anhydrous), germane, hexaethyl tetraphosphate, hydrogen azide, hydrogen cyanide, hydrogen selenide, hydrogen sulfide, hydrogen telluride, nickel tetracarbonyl, nitrogen dioxide, osmium tetroxide, oxygen difluoride, perchloryl fluoride, perfluoroisobutylene, phosgene, phosphine, phosphorus pentafluoride, selenium hexafluoride, silicon tetrachloride, silicon tetrafluoride, stibine, disulfur decafluoride, sulfur tetrafluoride, tellurium hexafluoride, tetraethyl pyrophosphate, tetraethyl dithiopyrophosphate, trifluoroacetyl chloride, or tungsten hexafluoride.

7. The method of claim 1, wherein the alerting device is a strobe light.

8. A detecting and alerting system for gases comprises:
a memory; and
at least one processor coupled with the memory and configured to:
determine a parts per million of a specified gas;
compare the determined parts per million to a pre-determined threshold;
when the determined parts per million meets or exceeds the pre-determined threshold, generate a control signal, transmit the control signal to an alerting device to emit an alert to a user; and
transmit the control signal to a control device, wherein the control device performs a specified task,
when the determined parts per million meets or exceeds a second threshold, transmit an additional control signal to a remote server;
wherein the remote server contacts emergency services,
wherein the pre-determined threshold is between 400 parts per million and 800 parts per million, and the second threshold is at or above 800 parts per million.

9. The system of claim 8, wherein the specified gas is carbon monoxide, and wherein the specified task comprises disabling an internal combustion engine located within a vehicle.

10. The system of claim 8, wherein the alerting device is a piezo buzzer.

11. The system of claim 8, wherein the parts per million is determined by a plurality of sensors, and wherein at least one sensor is located at a position where the specified gas is emitted.

12. The system of claim 8, wherein the specified task includes at least one of opening a window, turning on or off a HVAC system, opening a garage door, or shutting off a device emitting the specified gas.

13. The method of claim 8, wherein the specified gas is at least one of arsenic pentafluoride, arsine, bis(trifluoromethyl), boron tribromide, boron trichloride, boron trifluoride, bromine, bromine chloride, bromomethane, carbon monoxide, chlorine, chlorine pentafluoride, chlorine trifluoride, chloropicrin, cyanogen, cyanogen chloride, diazomethane, diborane, dichloroacetylene, dichlorosilane, fluorine, formaldehyde (anhydrous), germane, hexaethyl tetraphosphate, hydrogen azide, hydrogen cyanide, hydrogen selenide, hydrogen sulfide, hydrogen telluride, nickel tetracarbonyl, nitrogen dioxide, osmium tetroxide, oxygen difluoride, perchloryl fluoride, perfluoroisobutylene, phosgene, phosphine, phosphorus pentafluoride, selenium hexafluoride, silicon tetrachloride, silicon tetrafluoride, stibine, disulfur decafluoride, sulfur tetrafluoride, tellurium hexafluoride, tetraethyl pyrophosphate, tetraethyl dithiopyrophosphate, trifluoroacetyl chloride, or tungsten hexafluoride.

14. The system of claim 8, wherein the alerting device is a strobe light.

15. A non-transitory computer-readable storage medium containing executable computer program code, the code comprising instructions configured to cause a computing device to:
determine a parts per million of a specified gas;
compare the determined parts per million to a pre-determined threshold;
when the determined parts per million meets or exceeds the pre-determined threshold, generate a control signal, transmit the control signal to an alerting device to emit an alert to a user; and
transmit the control signal to a control device, wherein the control device performs a specified task,
when the determined parts per million meets or exceeds a second threshold, transmit an additional control signal to a remote server;
wherein the remote server contacts emergency services,
wherein the pre-determined threshold is between 400 parts per million and 800 parts per million, and the second threshold is at or above 800 parts per million.

16. The computer-readable medium of claim 15, wherein the specified gas is carbon monoxide, and wherein the specified task comprises disabling an internal combustion engine located within a vehicle.

17. The computer-readable medium of claim 15, wherein the alerting device is a piezo buzzer.

18. The computer-readable medium of claim 15, wherein the specified task includes at least one of opening a window, turning on or off a HVAC system, opening a garage door, or shutting off a device emitting the specified gas.

19. The method of claim 15, wherein the specified gas is at least one of arsenic pentafluoride, arsine, bis(trifluoromethyl), boron tribromide, boron trichloride, boron trifluoride, bromine, bromine chloride, bromomethane, carbon monoxide, chlorine, chlorine pentafluoride, chlorine trifluoride, chloropicrin, cyanogen, cyanogen chloride, diazomethane, diborane, dichloroacetylene, dichlorosilane, fluorine, formaldehyde (anhydrous), germane, hexaethyl tetraphosphate, hydrogen azide, hydrogen cyanide, hydrogen selenide, hydrogen sulfide, hydrogen telluride, nickel tetracarbonyl, nitrogen dioxide, osmium tetroxide, oxygen difluoride, perchloryl fluoride, perfluoroisobutylene, phosgene, phosphine, phosphorus pentafluoride, selenium hexafluoride, silicon tetrachloride, silicon tetrafluoride, stibine, disulfur decafluoride, sulfur tetrafluoride, tellurium hexafluoride, tetraethyl pyrophosphate, tetraethyl dithiopyrophosphate, trifluoroacetyl chloride, or tungsten hexafluoride.

20. The computer-readable medium of claim 15, wherein the alerting device is a strobe light.

* * * * *